United States Patent [19]

Sifniades et al.

[11] 4,123,446
[45] Oct. 31, 1978

[54] SYNTHESIS OF METAL ALKYL CARBONATES

[75] Inventors: Stylianos Sifniades, Madison; Allen A. Tunick, Boonton; Herbert C. Wohlers, Mountain Lakes, all of N.J.

[73] Assignee: Allied Chemical Corporation, Morris Township, Morris County, N.J.

[21] Appl. No.: 786,160

[22] Filed: Apr. 11, 1977

[51] Int. Cl.$^2$ ............................................. C07F 15/04
[52] U.S. Cl. .................................. 260/439 R; 260/463
[58] Field of Search ............................. 260/463, 439R

[56] References Cited

U.S. PATENT DOCUMENTS

| 3,445,497 | 5/1969 | Anderson et al. | 260/455 |
| 4,022,813 | 5/1977 | Neri et al. | 260/463 |

FOREIGN PATENT DOCUMENTS 2,555,567  6/1976  Fed. Rep. of Germany ........... 260/463

OTHER PUBLICATIONS

M. Stiles and H. Finkbeiner, JACS, 81, pp. 505-506; 2598-2599, (1969).
M. Stiles, Ann, N. Y., Acad. Sci., 88, pp. 332-340, (1970).
Fieser & Fieser, Reagents for Org. Synth., pp. 631-633, (1967).
Dow Chemical USA Applications Bulletins, "Dowex MWA-1," and Dowex Sar.

Primary Examiner—Lewis Gotts
Assistant Examiner—Molly C. Eakin
Attorney, Agent, or Firm—Robert J. North; Robert A. Harman

[57] ABSTRACT

A process is described for preparing metal alkyl carbonates, useful as carboxylating agents, which comprises reacting an inorganic metal salt with an aliphatic monohydric alcohol containing 1 to 3 carbon atoms and carbon dioxide under substantially anhydrous conditions in the presence of a solid acid acceptor, said alcohol being employed in sufficient amount to form a solution of the resulting metal alkyl carbonate in the alcohol.

11 Claims, No Drawings

SYNTHESIS OF METAL ALKYL CARBONATES

BACKGROUND OF THE INVENTION

1. Field of the Invention

This invention relates to the production of metal alkyl carbonates soluble in $C_1$-$C_3$ monhydric alcohols, useful as carboxylating agents.

2. Description of the Prior Art

Metal alkyl carbonates are known in the prior art as useful carboxylating agents for nitroalkanes and ketones, as shown in J. Am. Chem. Soc., Volume 81, pages 505 to 506, 2598 to 2599 (1969), Ann. New York Acad. Sci., Volume 88, pages 332 to 340 (1970), and "Reagents for Organic Synthesis", pages 631 to 633 by Fieser and Fieser (1967). The most important metal alkyl carbonate for use in carboxylation reactions is magnesium methyl carbonate (MMC) which is not normally isolated, but is generally prepared in methanol solution, the methanol then being replaced by a polar aprotic organic solvent in which carboxylation reactions can occur.

The methods of preparation of metal alkyl carbonates, soluble in monohydric alcohols containing 1 to 3 carbon atoms, such as MMC, described in the above references, either involve starting with expensive and hygroscopic metallic alkoxides such as magnesium methoxide and dissolving them in the appropriate alcohol, or forming them in situ by reacting an active metal, e.g. magnesium, with the appropriate alcohol, in which hydrogen is evolved as a by-product. Carbon dioxide is bubbled through the alcoholic solution of metallic alkoxide, prepared by either method, to form the metal alkyl carbonate. The alcohol is then replaced with a polar aprotic solvent, such as dimethylformamide. However, these methods suffer the disadvantages of either using expensive and moisture-sensitive starting reagents such as metallic alkoxides or the hazardous formation of the starting reagent in which flammable by-product hydrogen is evolved.

Another known procedure for producing metal alkyl carbonates is exemplified in U.S. Pat. No. 3,445,497 (1969, Anderson et al. to Signal Oil) in which a tertiary organic amine is reacted with carbon dioxide and alcohol to form an adduct, trialkylammonium alkyl carbonate, which is then reacted with an alcohol-soluble inorganic metal salt to form the metal alkyl carbonate in a reversible reaction. This process is useful for forming alcohol-insoluble metal alkyl carbonates in which the reversible reaction is carried to completion due to precipitation of the product from the reaction medium but is unsuitable for forming high yields of alcohol-soluble metal alkyl carbonates such as magnesium methyl carbonate (MMC) for use in subsequent carboxylation reactions. In the case of alcohol-soluble metal alkyl carbonates such as MMC, the above process is unsuitable since the reagent will not ordinarily function as a carboxylating agent in the presence of methanol, and cannot be transferred to methanol-free dimethylformamide solution without reverting to the original metal salt. This is due to the failure to remove the by-product acid present in solution as its trialkylammonium salt.

We have found that by-product acid, present as trialkylammonium salt, adversely interferes with the high yield production of alcohol-soluble metal alkyl carbonates, particularly MMC, by reversing the equilibrium reaction, and also that by-product acid causes an acid-catalyzed cleavage of the alcohol soluble metal alkyl carbonate when replacing the alcohol with a polar aprotic solvent prior to the carboxylation reaction.

It is, therefore, an object of this invention to provide a process for preparing metal alkyl carbonates, soluble in monohydric alcohols containing 1 to 3 carbon atoms, in high yield from inexpensive reagents, not involving hazardous process steps, which are free of by-product acid.

SUMMARY

In accordance with this invention, there is provided a process for preparing metal alkyl carbonates which comprises reacting an inorganic metal salt with an aliphatic monohydric alcohol containing 1 to 3 carbon atoms and carbon dioxide under substantially anhydrous conditions in the presence of a solid acid acceptor, said alcohol being employed in sufficient amount to form a solution of the resulting metal alkyl carbonate in the alcohol. A specific embodiment of this process employs magnesium chloride as the inorganic metal salt, methanol as the alcohol and a solid ion exchange resin containing tertiary alkylamine functionality as the solid acid acceptor.

DETAILED DESCRIPTION OF THE INVENTION AND PREFERRED EMBODIMENTS

It is believed that the reaction of this invention proceeds via the following equation:

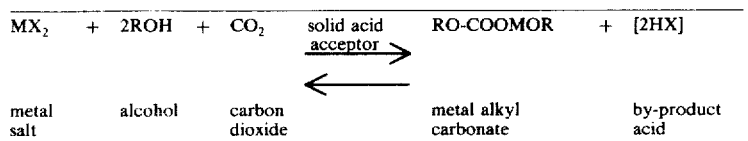

| $MX_2$ | + | 2ROH | + | $CO_2$ | $\xrightarrow{\text{solid acid acceptor}}$ | RO-COOMOR | + | [2HX] |
|---|---|---|---|---|---|---|---|---|
| metal salt | | alcohol | | carbon dioxide | | metal alkyl carbonate | | by-product acid | where M = metal cation, X = anion of an acid, R = alkyl containing 1 to 3 carbon atoms and HX = by-product acid which is thereafter bound to solid acid acceptor.

The process of this invention for the synthesis of metal alkyl carbonates, soluble in monohydric alcohols containing 1 to 3 carbon atoms, involves the removal of by-product acid from the reaction mixture by treatment with a solid acid acceptor, preferably a weakly basic ion exchange resin, thus shifting the equilibrium in the above reversible reaction to the right. This results in maximizing the yield of metal alkyl carbonate and also obviates any subsequent decomposition thereof accompanying the transfer of the metal alkyl carbonate reagent from the alcohol solution to a polar aprotic solvent.

The term, solid acid acceptor, refers to any alcohol-insoluble substance that possesses the ability to remove by-product acid from the alcohol solution without dissolving or forming water or alcohol-soluble by-products. Examples of useful acid acceptors are the basic ion exchange resins. Weakly or strongly basic ion exchange resins can be used to remove the by-product acid from solution. Generally, at least about 80%, and up to about 90% or higher of the by-product acid is removed by treating with the solid acid acceptor. It is preferred to use a weakly basic ion exchange resin because of the ease and economy of regeneration of the resin by washing with anhydrous methanol and ammonia.

Examples of weakly basic ion exchange resins which are applicable are the tertiary amine types, e.g. P—CH$_2$NR$_2$, wherein P denotes a polymer such as polystyrene or styrene-divinylbenzene copolymer and R is an alkyl group such as methyl wherein the trialkylamino group functions as an acid acceptor to form P—CH$_2$—NR$_2$·HX in which by-product acid, HX, is absorbed from the solution. A typical example of such a resin is Dowex MWA-1 (a trademark of Dow Chemical Co.).

Strongly basic ion exchange resins, which are applicable in the invention, for example, contain quaternary amino groups grafted onto the polystyrene polymer such as P—CH$_2$—NR$_3$$^+$OY$^-$ in which R is alkyl such as methyl and OY is the alkoxide portion of the alcohol used, e.g. CH$_3$O— where methanol is employed, which reacts with by-product acid HX to form the alcohol YOH and P—CH$_2$—NR$_3$$^+$X$^-$, thus removing by-product acid from solution.

The amount of resin used is generally in the range of 1.5 to 10 equivalents per equivalent of inorganic metal salt such as magnesium chloride, a preferred range being from about 1.7 to 2.1 equivalents. Larger amounts of resin can be used but it is uneconomical to do so. The resin can be used directly in a batch-type reaction being present with the inorganic metal salt and carbon dioxide to form the metal alkyl carbonate, but it is more desirable to utilize the resin in a column, wherein the efficiency of the resin in removing by-product acid is greatly enhanced. Thus, the preferred mode of operation is to prepare an anhydrous alcohol solution of the inorganic metal salt, saturate the solution with carbon dioxide, and then treat the solution by eluting through a column containing the resin in anhydrous alcohol under applied carbon dioxide pressure. In this manner, yields of 80 to 95 percent of the metal alkyl carbonate are formed based on the amount of metal salt used.

The inorganic metal salts which are applicable in the instant invention are generally metallic salts of weak or strong acids. The requirements of the salt used are that, (1) it must be soluble in a monohydric aliphatic alcohol containing 1 to 3 carbon atoms, (2) the salt must be capable of forming an alcohol-soluble metal alkyl carbonate, and (3) it must be substantially anhydrous. Typical metals that function as the cation in the metal salt are magnesium and nickel, and it is preferred to use magnesium as the metal cation.

Typical anions which can be used in the metal salt are: (1), those derived from strong acids such as fluoride, nitrate, sulfate, bromide, iodide, chlorate, and perchlorate; and (2), those derived from weak acids such as acetate and benzoate. It is preferred to use anions of the strong acids that do not contain an acidic replaceable hydrogen such as HSO$_4$$^-$ and H$_2$PO$_4$$^=$, such that a weakly basic ion exchange resin can be employed to efficiently remove by-product acid, and it is preferred to use chloride ion as the anion in the salt.

Examples of salts that are applicable in the invention are magnesium chloride, magnesium iodide, magnesium bromide, magnesium nitrate, magnesium acetate, nickel acetate, nickel chloride, nickel bromide and nickel iodide. It is preferred, however, to use anhydrous magnesium chloride.

Alcohols which are applicable in the invention are the monohydric aliphatic alcohols containing 1 to 3 carbon atoms which include methanol, ethanol, propanol and isopropanol. The alcohol forms the alkyl portion of the metal alkyl carbonate, and it is preferred to use methanol such that the metal alkyl carbonate formed is a metal methyl carbonate.

The amount of alcohol used is generally the minimum amount needed to dissolve the starting metal salt, and is usually at least about 1.6 parts, preferably at least about 10 parts, by weight of alcohol per part of metal salt. The amount of alcohol necessary to dissolve the starting metal salt is sufficient to form a solution of the resulting metal alkyl carbonate and to avoid precipitation of metal alkyl carbonate or metal salt when eluting the alcohol solution of reagents through the ion exchange column. The alcohol used must be substantially anhydrous. By this term is meant that the alcohol has a water content of no more than 0.05 percent by weight. Use of alcohol having a water content below 0.01 percent is preferred.

Also contemplated within the scope of this invention is replacement of a minor amount of the alcohol with an organic co-solvent. Suitable organic co-solvents must be soluble in the alcohol used and typically comprise the N,N-dialkylamides of monocarboxylic acids, dialkyl sulfoxides, N-alkyl-2-pyrrolidones and hexa-alkyl phosphorotriamides, where the co-solvent functions to reduce the amount of alcohol required in the invention without interfering in the formation of the metal alkyl carbonate, in the subsequent removal of the alcohol and replacement by an aprotic solvent or in the subsequent carboxylation reaction. Preferred solvents for this purpose are dimethylformamide and dimethylacetamide and particularly preferred is dimethylformamide. The amount of such co-solvent used is generally up to about 25% by weight of the alcohol and preferably up to about 10% by weight of the alcohol.

The carbon dioxide used is generally gaseous in form rather than solid, since the gaseous form can be obtained in substantially anhydrous form. In general, the carbon dioxide is bubbled into the alcohol solution of the metal salt under pressure in order to preferably saturate the solution with carbon dioxide. Generally a pressure value of 15 to 100 psia is utilized for the saturation step, although higher pressures can be utilized. The molar ratio of carbon dioxide to metal salt used is at least about 1:1, but generally it is preferred to use a ratio of about 2 to 10:1. When eluting the carbon dioxide saturated alcohol solution of metal salt through the column, it is preferred to use anhydrous carbon dioxide under pressure at a value of about 40 psig (about 55 psia).

The temperature of the reaction is not critical and is generally carried out at about room temperature to obtain efficient saturation of the alcohol solution of metal salt by carbon dioxide. However, a higher temperature, up to the boiling point of the alcohol or co-solvent mixture, may be used initially to dissolve the metal salt in the alcohol followed by cooling to allow efficient saturation with carbon dioxide. The removal of by-product acid when eluting through a column is generally carried out at about room temperature, but a temperature of up to 80° C may utilized to increase the rate of the exchange reaction.

The time of elution of the alcohol solution of metal salt saturated with carbon dioxide through the column is a function of the temperature, the size of the column and the amount of resin used. In general, an elution rate suffficiently slow to maximize removal of by-product acid from the solution is preferred.

After the ion-exchange column has been used, it can be regenerated for further use by washing it with anhydrous ammonia in methanol in the case of a weakly basic ion exchange resin to remove by-product acid, and in this manner a cyclic process can be achieved. If a strongly basic resin is used, the regeneration may be carried out by washing with a strong base, e.g. lithium methoxide.

The use of metal alkyl carbonates is well known in the art for the carboxylation of various organic ketones and nitro compounds. For the subsequent carboxylation reaction, the alcohol solution of metal alkyl carbonate is modified by the substitution of a polar aprotic solvent such as dimethylformamide for the alcohol which is removed from the solution by distillation, resulting in a substantially anhydrous and alcohol-free solution of the metal alkyl carbonate in the polar aprotic solvent. The utility of these polar aprotic solutions of metal alkyl carbonates for use in subsequent carboxylations of ketones is well known. In addition to known utility, a dimethylformamide solution of MMC can be used for the dicarboxylation of acetone to produce acetone dicarboxylic acid, which is a useful intermediate in the synthesis of citric acid.

The following examples are not to be construed as limitations on the scope and spirit of the instant invention. Parts given are by weight unless otherwise indicated, and yields of metal alkyl carbonates are based on the amount of metal salt charged.

EXAMPLE 1

A solution of 3.34 parts anhydrous magnesium chloride in 180 parts anhydrous methanol was saturated with dry carbon dioxide gas and passed under 40 psig carbon dioxide pressure through a chromatographic column containing 94.7 parts of Dowex MWA-1 weakly basic anion exchange resin in the free base form in methanol. A total of about 320 parts of methanol, including carbon dioxide saturated methanol rinses, was passed through the column at a rate of about 2 parts of solution/min. Analysis of the eluted methanol solution by titrations for chloride ion using silver nitrate and base content using sulfuric acid, showed that magnesium methyl carbonate was formed in a 91.5 percent yield of theory.

The resin in the above example was regenerated by first rinsing with 120 parts carbon dioxide free anhydrous methanol, then passing through 320 parts, 1.9 molar ammonia in anhydrous methanol. The resin was then rinsed with 320 parts dry methanol to remove all ammonia. Analysis of the combined methanol rinses by titration for chloride ion showed that over 90 percent of the by-product acid formed during the formation of magnesium methyl carbonate was removed by the resin.

EXAMPLE 2

The procedure of Example 1 was repeated using instead 4.86 parts anhydrous magnesium chloride in about 200 parts methanol. Analysis of the eluted methanol solution by titrations for chloride ion and base content, showed that magnesium methyl carbonate was formed in an 84.6 percent yield of theory.

EXAMPLE 3

The procedure of Example 1 was repeated using dry nitrogen instead of carbon dioxide. Analysis of the eluted methanol solution by titrations for chloride ion and base content, showed that only a maximum of 6.2 percent of chloride was replaced by methoxide, indicating that elution under carbon dioxide is necessary for high yields.

EXAMPLE 4

The procedure of Example 1 was repeated using an equivalent amount of anhydrous nickel chloride instead of magnesium chloride. Analysis of the eluted methanol solution by titrations for chloride ion and base content, showed that nickel methyl carbonate had been formed in a 98.8 percent yield of theory.

EXAMPLE 5

Carboxylation of Acetone

To the methanolic solution of MMC made by the procedure of Example 1 were added 0.32 parts of sodium methoxide which was equivalent to the residual chloride present in that solution. Anhydrous dimethylformamide, 25 parts, was added to the mixture and methanol was removed by distillation. The residue was filtered to remove sodium chloride, 0.18 parts, producing an essentially methanol-free solution of MMC in dimethylformamide. Twenty parts of this solution was placed in a stainless steel autoclave along with 0.269 part acetone, and the autoclave was pressurized with dry nitrogen to 200 psig. The autoclave was heated to 130° C for 3 hours while the contents were stirred magnetically. Analysis for acetone dicarboxylic acid and acetoacetic acid by the method of Nebbia and Belotti, [Chim. Indust., Vol. 52,791 (1970)], showed 0.413 part (61.4 percent yield of theory) acetone dicarboxylic acid and 0.113 part (24.0 percent yield of theory) acetoacetic acid.

We claim:

1. A process for preparing metal alkyl carbonates which comprises reacting an inorganic metal salt with an alkyl monohydric alcohol containing 1 to 3 carbon atoms and carbon dioxide under substantially anhydrous conditions in the presence of a solid acid acceptor, said salt being soluble in said alcohol and said alcohol being employed in sufficient amount to form a solution of the resulting metal alkyl carbonate in the alcohol.

2. The process of claim 1 wherein the acid acceptor is a basic ion exchange resin.

3. The process of claim 2 wherein the basic ion exchange resin is a weakly basic ion exchange resin comprised of a solid polymer having tertiary alkylamine groups affixed thereto.

4. The process of claim 1 wherein the weight ratio of alcohol to metal salt is at least about 1.6:1.

5. The process of claim 1 wherein the reaction is conducted under pressure with carbon dioxide.

6. The process of claim 1 wherein the metal salt is magnesium chloride.

7. The process of claim 1 wherein the metal salt is nickel chloride.

8. The process of claim 1 wherein the alcohol is methanol.

9. The process of claim 1 wherein up to about 25% by weight of the alcohol is replaced by an organic co-solvent soluble in said alcohol.

10. The process of claim 1 wherein the inorganic metal salt is magnesium chloride, the alcohol is methanol and the resulting metal alkyl carbonate is magnesium methyl carbonate.

11. The process of claim 1 wherein the inorganic metal salt is nickel chloride, the alcohol is methanol and the resulting metal alkyl carbonate is nickel methyl carbonate.

* * * * *